United States Patent [19]
Woo

[11] Patent Number: 5,603,951
[45] Date of Patent: Feb. 18, 1997

[54] CYCLOSPORIN-CONTAINING SOFT CAPSULE COMPOSITIONS

[75] Inventor: Jong S. Woo, Kyunggi-do, Rep. of Korea

[73] Assignee: Hanmi Pharm. Ind. Co., Ltd., Kyunggi-do, Rep. of Korea

[21] Appl. No.: 427,190

[22] Filed: Apr. 21, 1995

[30] Foreign Application Priority Data

Nov. 9, 1994 [KR] Rep. of Korea .................. 94-29208

[51] Int. Cl.$^6$ .................................................. A61K 9/48
[52] U.S. Cl. .................... 424/455; 424/452; 514/975; 514/970
[58] Field of Search .................... 424/455, 452, 424/451, 456

[56] References Cited

U.S. PATENT DOCUMENTS

| | | | |
|---|---|---|---|
| 4,388,307 | 6/1983 | Cavanak | 424/408 |
| 4,817,367 | 4/1989 | Ishikawa et al. | 53/454 |
| 4,895,725 | 1/1990 | Kantor et al. | 424/455 |
| 4,970,076 | 11/1990 | Horrobin | 424/456 |
| 5,098,606 | 3/1992 | Nakajima et al. | 424/450 |
| 5,338,761 | 8/1994 | Nakajima et al. | 514/772 |

FOREIGN PATENT DOCUMENTS

| | | |
|---|---|---|
| 649651 | 4/1995 | European Pat. Off. |
| 90-4348 | 4/1990 | Rep. of Korea |
| 2228198 | 2/1990 | United Kingdom |

OTHER PUBLICATIONS

Zia et al., *Chemical Abstracts*, vol. 114, #214309, Jan. 1991.

Primary Examiner—Thurman K. Page
Assistant Examiner—James M. Spear
Attorney, Agent, or Firm—Lowe, Price, LeBlanc & Becker

[57] ABSTRACT

The present invention relates to a soft capsule composition containing a stable microemulsion concentrate which is more stable and suitable for the preparation of cyclosporin-containing soft capsules. More specifically, the present invention relates to a microemulsion concentrate containing cyclosporin as an active ingredient, dimethylisosorbide as a co-surfactant, one component or a mixture of two or more selected from the group consisting of an esterified compound of fatty acid and primary alcohol, medium chain fatty acid triglyceride and monoglyceride as an oil component, and a surfactant having HLB value of 10 to 17, such as Nikkol HCO-50 or Tween 20, which is suitable for formulation into soft capsules and to a soft capsule composition containing said microemulsion concentrate. In the microemulsion concentrate according to the present invention, cyclosporin, dimethylisosorbide, the oil component and the surfactant are present in the ratio of 1:11–5:1–5:3–6, preferably 1:3–4:1.5–3:4–6, and particularly 1:3.6:2.6:5.5, by weight.

19 Claims, 3 Drawing Sheets

CYCLOSPORIN-CONTAINING SOFT CAPSULE COMPOSITIONS

BACKGROUND OF THE INVENTION

1. Field of the Invention

The present invention relates to a soft capsule composition containing a stable microemulsion concentrate which is more stable and suitable for the preparation of cyclosporin-containing soft capsules. More specifically, the present invention relates to a microemulsion concentrate containing cyclosporin as an active ingredient, dimethylisosorbide as a cosurfactant, one component or a mixture of two or more selected from the group consisting of an esterified compound of fatty acid and primary alcohol, medium chain fatty acid triglyceride and fatty acid monoglyceride as an oil component, and a surfactant having HLB (Hydrophilic-lipophilic balance) value of 10 to 17 such as Nikkol HCO-50 or Tween 20, which is suitable for formulation into soft capsules and to a soft capsule composition containing said microemulsion concentrate.

2. Background Art

Cyclosporin is a specific macromolecular (molecular weight 1202.64) cyclic peptide compound consisting of 11 amino acids, which has a broad spectrum of useful pharmacological activities, particularly immuno-suppressive activity and anti-inflammatory activity. Therefore, cyclosporin has been used for suppression of inherent immunological responses of the living body, which are caused by tissue and organ transplantation, for example, transplantation of the heart, lung, liver, kidney, pancreas, bone marrow, skin and cornea, and especially the transplantation of foreign tissues and organs. In addition, cyclosporin is useful for the suppression of hematological disorders such as anemia, various autoimmune diseases such as systemic lupus erythematosus, idiopathic malabsorption syndrom, etc., and inflammatory diseases such as arthritis, rheumatoid disorder, etc. Cyclosporin is also useful in treatment of protozoal diseases such as malaria, schistosomiasis, etc., and furthermore, recently it is partly used in chemotherapy.

Cyclosporin is highly lipophilic and hydrophobic with a solubility in water at 25° C. being 16 to 23 mg of cyclosporin per liter of water. On the other hand, cyclosporin is well dissolved in an organic solvent such as methanol, ethanol, acetone, ether, chloroform and the like, due to its high lipophilic property. Due to low water-solubility of cyclosporin having above mentioned properties, when cyclosporin is administered orally, its bioavailability is extremely low and may be greately influenced by the condition of each individual patient. Accordingly, it is very difficult to retain an effective therapeutic concentration. Moreover, cyclosporin may shows considerable side effects such as nephrotoxicity. Thus, cyclosporin is very difficult to formulate into a preparation for oral administration due to its low water solubility. Accordingly, numerous studies have been extensively conducted to find a preparation suitable for the effective oral administration of cyclosporin, which can provide a suitable uniform dosage and appropriate bioavailability.

The prior art preparations suitable for oral administration of sparingly water-soluble cyclosporin are usually formulated in the form of a microemulsion by combining cyclosporin with a surfactant, an oil and a cosurfactant.

One typical method using this combination is taught in U.S. Pat. No. 4,388,307 which is issued on Jun. 14, 1983. This patent discloses a liquid formulation of cyclosporin using ethanol as a cosurfactant. According to the method disclosed in this U.S. Patent Specification, cyclosporin is combined with a carrier consisting of ethanol as a cosurfactant, olive oil as a vegetable oil, and a transesterification product of a natural vegetable oil triglyceride and a polyalkylene polyol as a surfactant to form the liquid formulation. However, the resulting liquid formulation is administered as an aqueous dilution which makes it very difficult to adapt the subjects to its administration and to provide a uniform dosage for oral administration.

In order to mitigate the inconvenience of diluting the cyclosporin liquid composition in water prior to oral administration, a liquid composition in the form of a microemulsion concentrate has been formulated into a soft capsule preparation, which is now commercially available as Sandimmun$^R$ (trademark). In this preparation, the cyclosporin soft capsule contains a large amount of ethanol as a cosurfactant due to the solubility requirements of cyclosporin. However, since ethanol, which has a low boiling point, permeates the gelatin membrane of the capsule to volatilize even at normal temperature, the content of ethanol is reduced and the constitutional ratio of the contents in soft capsules varies during storage. The reduced ethanol content results in crystallization of cyclosporin and a significant difference in the bioavailability of cyclosporin. Thus, it make the determination of dosage of cyclosporin which can provide a suitable therapeutic effect difficult.

In an effort to prevent the volatilization of ethanol from the soft capsule preparations during storage and distribution, the soft capsule preparations are wrapped in a special packing material, such as an aluminum film foam package. However, such specific packaging does not completely maintain the uniform composition of the wrapped capsule. It has been demonstrated through experiments that although the cyclosporin soft capsule is wrapped up in aluminum film foam package, the ethanol content is lowered to 7.9% from the initial level of 10.8% after a period of one week. This results in a great difference in bioavailability of cyclosporin and may contribute to the price increase.

To solve the above-mentioned disadvantages which accompany the use of ethanol as a cosurfactant, a method using a non-ethanol component as a cosurfactant has been proposed. For example, British Laid-open Patent Publication No. 2,228,198 (Feb. 16, 1990) discloses a method for increasing stability and bioavailability of cyclosporin preparations by containing a vegetable oil triglyceride of saturated fatty acid such as caprylic/capric acid triglyceride [trade mark: MIGLYOL 812] or linolenic acid monoglyceride [trade mark: MYVEROL 18-92] as an oil component and a surfactant having HLB (Hydrophilic-lipophilic balance) value of 10 or more, particularly a reaction product of castor oil and ethylene oxide [trade mark: CREMOPHOR RH 40]. In addition, Korean Laid-open Patent Publication No. 90-4348 (Apr. 12, 1990) discloses a pharmaceutical composition in the form of a microemulsion concentrate containing a non-ethanol component which is selected from pharmaceutically acceptable $C_{1-5}$ alkyl or tetrahydrofurfuryl di- or partial-ether of low molecular mono- or poly-oxyalkanediol, for example, diethyleneglycol monoethyl ether [trade mark: TRANSCUTOL] or tetrahydrofurfuryl alcohol polyethylene glycol [trade mark: GLYCOFUROL] and 1,2-propyleneglycol as a cosurfactant, a medium chain fatty acid triglyceride, particularly caprylic/capric acid triglyceride [trade mark: MIGLYOL 812], as an oil component, and a reaction product of castor oil and ethylene oxide [trade mark: CREMOPHOR RH 40] as a surfactant. Such soft capsule formulations result in somewhat increasing in bioavailability of cyclosporin in comparison with prior commercial cyclosporin preparations. However, the above non-ethanol cosurfactants are glycols which contain the —OH group in their structures. It has now been identified that the OH group-containing glycol creates problems in the formulation of soft capsules because its strong absorption property is sufficient to absorb the moisture from the atmosphere and also because it is highly permeable to the gelatin film of the soft capsule.

Under such conditions, the present inventors studied numerous additives, including various solvents, in an effort to find a cosurfactant capable of providing a microemulsion concentrate suitable for the formulation of cyclosporin into a soft capsule preparation. As a result, a certain pharmaceutically acceptable solvent, dimethylisosorbide [trade mark: Arlasove$^R$ DMI, available from ICI Speciality Chemicals] has been found as a suitable solvent for this purpose. Thus, a cyclosporin preparation containing dimethylisosorbide as a cosurfactant is the subject of other pending patent application [Korean Patent Application No. 94-13945 filed on Jun. 20, 1994]. In this patent application, the present inventors disclose a microemulsion concentrate containing cyclosporin in combination with a carrier consisting of dimethylisosorbide as a cosurfactant, refined fish oil as an oil component and a surfactant, which is suitable for formulation into soft capsules for oral administration and a soft gelatin capsule composition containing such microemulsion concentrate. Since dimethylisosorbide which is used as a cosurfactant in this formulation has a high boiling point, 234° C., it does not volatilize even at high temperature such as the temperature necessary for manufacturing soft capsules. In addition, dimethylisosorbide does not contain any hydroxy groups, —OH, and therefore, its hygroscopic property is very low and it does not permeate the gelatin membrane and dissolves cyclosporin well. Refined fish oil is ideally fit for the absorption of cyclosporin since it contains a highly saturated fatty acid such as EPA (eicosapentaenoic acid) and DHA (docosahexaenoic acid). Accordingly, the soft gelatin capsule composition containing this microemulsion concentrate exhibits a blood level of cyclosporin comparable to that of the prior art ethanol-containing soft capsule preparation when they are orally administered and is stably maintained without any change over a prolonged storage period. Thus, it provides a significant improvement in the field of preparation of the cyclosporin soft capsules.

However, recently it has been required to develope a cyclosporin preparation which has a stability during the storage period and further provides substantially no difference in biological availability and its variable factors between individual subjects. One of the preparations developed for this purpose is disclosed in Korean Laid-open Patent Publication No. 93-113. However, since this preparation uses ethanol as a cosurfactant, it has some disadvantages like as in the prior ethanol-containing preparations, that is, the storage stability is poor, and the ethanol content is changed to cause the precipitation of cyclosporin and the lowering of cyclosporin bioavailability.

Accordingly, the present inventors have studied numerous combinations of various surfactants and oil components to find a cyclosporin preparation which is stable, and provides higher bioavailability and lower difference in blood levels between individual subjects than those of the prior cyclosporin preparations in view of their pharmacokinetic properties. As a result, we have identified that a certain cyclosporin composition consisting of the components as defined below can satisfy the above-mentioned requirement, and then completed the present invention.

Therefore, it is an object of the present invention to provide a microemulsion concentrate containing cyclosporin, dimethylisosorbide as a cosurfactant, and an oil component and a surfactant, as specifically defined below, which is suitable for formulation into soft capsules for oral administration.

It is a further object of the present invention to provide a microemulsion concentrate suitable for formulation into soft capsules, which contains cyclosporin as an active ingredient, dimethylisosorbide as a cosurfactant, one component or a mixture of two or more components selected from the group consisting of an esterified compound of fatty acid and primary alcohol, medium chain fatty acid triglyceride and fatty acid monoglyceride as an oil component, and a surfactant having HLB (Hydrophilic-lipophilic balance) value of 10 to 17.

Further, it is another object of the present invention to provide a soft gelatin capsule composition according to the present invention which is highly storage stable such that there is little variation of the composition over time, and has an increased bioavailability.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention and the drawings, in addition to the scope of the invention defined by the claims.

BRIEF DESCRIPTION OF THE DRAWINGS

For a thorough understanding of the nature and objects of the invention, reference should be had to the following detailed description taken in connection with the accompanying drawings in which.

DISCLOSURE OF INVENTION

In one aspect, the present invention relates to a microemulsion concentrate comprising cyclosporin as an active ingredient, dimethylisosorbide as a cosurfactant, an oil component and a surfactant, as specifically defined below, which is suitable for formulation into soft capsules for oral administration.

More specifically, the present invention relates to a microemulsion concentrate suitable for formulation into soft capsules, which contains cyclosporin as an active ingredient, dimethylisosorbide as a cosurfactant, one component or a mixture of two or more components selected from the group consisting of an esterified compound of fatty acid and primary alcohol, medium chain fatty acid triglyceride and fatty acid monoglyceride as an oil component, and a surfactant having HLB (Hydrophilic-lipophilic balance) value of 10 to 17.

Cyclosporin, which is used as the pharmaceutically active ingredient in the microemulsion concentrate according to the present invention, is a cyclic peptide compound having useful immuno-suppressive activity and anti-inflammatory activity as described above. Although cyclosporin A, B, C, D, G and the like can be used as the cyclosporin component in the present invention, cyclosporin A is mostly preferred since its clinical effectiveness and pharmacological properties are well established in the art.

As the cosurfactant, which is the second essential component in the microemulsion concentrate according to the present invention, dimethylisosorbide [trade mark: ARLA-SOLVE$^R$ DMI, ICI Speciality Chemicals], which is non-volatile, does not permeate the gelatine membrane of the soft capsule, has low hygroscopic property and is a solvent having a high solubility for cyclosporin, is used.

In the present invention, the use of dimethylisosorbide as a cosurfactant in the microemulsion concentrate provides certain advantages. That is, when the microemulsion concentrate is formulated into a soft capsule, the stability of the composition during storage is improved and therefore the contents of the components contained therein are substantially uniformly maintained so that the uniformity of the composition content can be assured over a greater time period than ethanol based compositions.

In the microemulsion concentrate of the present invention, dimethylisosorbide is used preferably in the ratio of 1 to 5 parts by weight, more preferably 3 to 4 parts by weight, and most preferably 3.6 parts by weight, per 1 part by weight of cyclosporin.

The third component used in the microemulsion concentrate according to the present invention is an oil(s). As the oil component in the present invention, one component or a mixture of two or more components selected from the group consisting of esterified compounds of fatty acid and primary alcohol, medium chain fatty acid triglycerides and fatty acid monoglycerides can be used. The esterified compound of fatty acid and primary alcohol which can be used in the present invention may include an esterified compound of fatty acid having 8 to 20 carbon atoms and primary alcohol having 2 to 3 carbon atoms, for example, isopropyl myristate, isopropyl palmitate, ethyl linoleate, ethyl oleate, etc., with an esterified compound of linolenic acid and ethanol [trade mark: NIKKOL VF-E, Nikko Chemicals Co., Ltd., Japan] being preferable. In addition, as the medium chain fatty acid triglyceride a triglyceride of saturated fatty acid having 8 to 10 carbon atoms can be used with caprylic/capric acid triglyceride [trade mark: MIGLYOL 812] which is a vegetable oil triglyceride of saturated fatty acid being most preferably used. The fatty acid monoglyceride which can be preferably used as the oil component in the present invention includes a monoglyceride of fatty acid having 18 to 20 carbon atoms, particularly monoglyceride of oleic acid [trade mark: MONOMULS 90-018, Henkel].

In the present invention, although one component selected from the above exemplified oil components can be singly used, a mixture of at least two oils selected therefrom, particularly a mixture of two or three fatty acid ester compounds can be preferably used. In the microemulsion concentrate according to the present invention, the oil component is used in the ratio of 1 to 5 parts by weight, preferably 1.5 to 3 parts by weight, per 1 part by weight of cyclosporin. Most preferably, the oil component is used in the ratio of 2.6 parts by weight per 1 part by weight of cyclosporin. When the mixture of oil components as mentioned above is used in the composition according to the present invention, the mixing ratio of an esterified compound of fatty acid and primary alcohol: medium chain fatty acid triglyceride: fatty acid monoglyceride can be in the range of 1:0.1–1.0:0–1.0, preferably in the range of 1:0.12–0.50:0–0.50 and particularly 1:0.25:0.375, on the basis of weight. In addition, the constitutional ratio of fatty acids, i.e. caprylic acid: capric acid: palmitic acid: oleic acid: linolenic acid ricinoleic acid in such oil mixture is preferably in the range of 3–7:3–7:5–8:15–25:40–50:3–10.

The fourth essential component used in the microemulsion concentrate according to the present invention is a surfactant. The suitable surfactants for use in the present invention include any of pharmaceutically acceptable surfactants having HLB (Hydrophilic-lipophilic balance) value of 10 to 17, which are capable of stably emulsifying the lipophilic portion of the composition comprising the cyclosporin-containing oil component and the hydrophilic portion comprising the cosurfactant in water to form a stable microemulsion. Examples of the preferred surfactants according to the present invention include polyoxyethylene products of hydrogenated vegetable oils, peolyoxyethylene-sorbitan-fatty acid esters, and the like, for example, NIKKOL HCO-50, NIKKOL HCO-40, NIKKOL HCO-60, TWEEN 20, TWEEN 21, TWEEN 40, TWEEN 60, TWEEN 80, TWEEN 81, etc. Particularly, a polyoxyethylene (50) hydrogenated castor oil which is commercialized under the trade mark NIKKOL HCO-50 (Nikko Chemical Co., Ltd.) having an acid value below 1, a saponification value of about 48–56, a hydroxyl value of about 45–55 and pH value (5%) of 4.5–7.0, and a polyoxyethylene (20) sorbitan monolaurate which is commercialized under the trade mark TWEEN 20 (ICI Chemicals) can be preferably used.

The surfactant can include any one of the above-mentioned surfactants alone or, preferably, in a combination of two or more surfactants selected from the above surfactants. In the microemulsion concentrate according to the present invention, the surfactants can be used in the ratio of 3 to 6 parts by weight, preferably in the ratio of 4 to 6 parts by weight and particularly in the ratio of 5.5 parts by weight, per 1 part by weight of cyclosporin. In addition, when the mixture of two surfactants, i.e. polyoxyethylene (50) hydrogenated castor oil and polyoxyethylene (20) sorbitan monolaurate is used in the microemulsion concentrate of the present invention, the constitutional ratio of polyoxyethylene (50) hydrogenated castor oil: polyoxyethylene (20) sorbitan monolaurate is preferably in the range of 1:0.5–2, more preferably in the range of 1:0.7–1.5, and most preferably in the range of 1:1.0.

In the microemulsion concentrate according to the present invention, four essential components are present preferably in the ratio of cyclosporin: cosurfactant: oil component: surfactant =1:1–5:1–5:3–6, and more preferably in the ratio of cyclosporin: cosurfactant: oil component: surfactant= 1:3–4:1.5–3:4–6 by weight. The most preferable microemulsion concentrate according to the present invention consists of cyclosporin, dimethylisosorbide, oil component and surfactant in the ratio of 1:3.6:2.6:5.5 by weight. In addition to this composition, the composition illustrated in the following examples can be mentioned as the further preferable compositions according to the present invention.

For oral administration, the microemulsion concentrate having the above-mentioned composition, according to the present invention, can be formulated into the form of a soft capsule. In formulating the soft capsule, the capsule preparation can further contain, if necessary, pharmaceutically acceptable adjuvants, excipients and additives which are conventionally utilized in the preparation of soft capsules, in addition to the above microemulsion concentrate. Such additives include, for example, lecithin, viscosity regulator, perfume (e.g. peppermint oil, etc.), antioxidant (e.g. tocopherol, etc.), preservative (e.g. parabens, etc. ), coloring agent, glycerin, sorbitol, gelatin, etc.

The soft capsule preparation according to the present invention can be prepared according to conventional methods for the preparation of soft capsules. For example, cyclosporin is first dissolved in dimethylisosorbide while gently warming at the temperature of approximately 60° C. The oil component and the surfactant are then added to the resulting mixture and the whole mixture is uniformly mixed. The resulting microemulsion concentrate is then introduced into a machine for preparing soft capsules, with or without the above-mentioned pharmaceutically acceptable additives conventionally utilized in preparation of soft capsules, to prepare the desired suitable cyclosporin soft capsule.

The present invention will be more specifically illustrated by the following examples. However, it should be understood that the present invention is not limited by these examples in any manner.

| | Component | Content (mg/Cap.) |
|---|---|---|
| Example 1 | | |
| 1-1. | Cyclosporin | 25 |
| | Dimethylisosorbide(Arlasolve$^R$ DMI) | 90 |
| | TWEEN 20 | 42 |
| | NIKKOL HCO-50 | 68 |
| | NIKKOL VF-E | 40 |
| | MIGLYOL 812 | 10 |
| | MONOMULS 90-018 | 15 |
| | Total | 290 mg |
| 1-2. | Cyclosporin | 25 |
| | Dimethylisosorbide(Arlasolve$^R$ DMI) | 90 |
| | TWEEN 20 | 70 |
| | NIKKOL HCO-50 | 68 |
| | NIKKOL VF-E | 40 |
| | MIGLYOL 812 | 10 |
| | MONOMULS 90-018 | 15 |
| | Total | 318 mg |
| 1-3. | Cyclosporin | 25 |
| | Dimethylisosorbide(Arlasolve$^R$ DMI) | 90 |
| | TWEEN 20 | 42 |
| | NIKKOL HCO-50 | 68 |
| | NIKKOL VF-E | 40 |
| | MIGLYOL 812 | 10 |
| | Total | 275 mg |
| 1-4. | Cyclosporin | 25 |
| | Dimethylisosorbide(Arlasolve$^R$ DMI) | 90 |
| | TWEEN 20 | 42 |
| | NIKKOL HCO-50 | 68 |
| | NIKKOL VF-E | 40 |
| | Total | 265 mg |
| 1-5. | Cyclosporin | 25 |
| | Dimethylisosorbide(Arlasolve$^R$ DMI) | 90 |
| | NIKKOL HCO-50 | 68 |
| | NIKKOL VF-E | 40 |
| | Total | 223 mg |
| Example 2 | | |
| 2-1. | Cyclosporin | 25 |
| | Dimethylisosorbide(Arlasolve$^R$ DMI) | 25 |
| | TWEEN 20 | 42 |
| | NIKKOL HCO-60 | 68 |
| | NIKKOL VF-E | 40 |
| | MIGLYOL 812 | 10 |
| | MONOMULS 90-018 | 15 |
| | Total | 225 mg |
| 2-2. | Cyclosporin | 25 |
| | Dimethylisosorbide(Arlasolve$^R$ DMI) | 50 |
| | TWEEN 20 | 42 |
| | NIKKOL HCO-50 | 68 |
| | NIKKOL VF-E | 40 |
| | MIGLYOL 812 | 10 |
| | Monomuls 90-018 | 15 |
| | Total | 250 mg |
| 2-3. | Cyclosporin | 25 |
| | Dimethylisosorbide(Arlasolve$^R$ DMI) | 100 |
| | TWEEN 20 | 42 |
| | NIKKOL HCO-50 | 68 |
| | NIKKOL VF-E | 40 |
| | MIGLYOL 812 | 10 |
| | MONOMULS 90-018 | 15 |
| | Total | 300 mg |
| 2-4. | Cyclosporin | 25 |
| | Dimethylisosorbide(Arlasolve$^R$ DMI) | 120 |
| | TWEEN 20 | 42 |
| | NIKKOL HCO-50 | 68 |
| | NIKKOL VF-E | 40 |
| | MIGLYOL 812 | 10 |
| | MONOMULS 90-018 | 15 |
| | Total | 320 mg |
| Example 3 | | |
| 3-1. | Cyclosporin | 25 |
| | Dimethylisosorbide(Arlasolve$^R$ DMI) | 90 |
| | TWEEN 20 | 40 |
| | NIKKOL HCO-50 | 40 |
| | NIKKOL VF-E | 40 |
| | MIGLYOL 812 | 10 |
| | MONOMULS 90-018 | 15 |
| | Total | 260 mg |
| 3-2. | Cyclosporin | 25 |
| | Dimethylisosorbide(Arlasolve$^R$ DMI) | 90 |
| | TWEEN 20 | 30 |
| | NIKKOL HCO-50 | 60 |
| | NIKKOL VF-E | 40 |
| | MIGLYOL 812 | 10 |
| | MONOMULS 90-018 | 15 |
| | Total | 270 mg |
| 3-3. | Cyclosporin | 25 |
| | Dimethylisosorbide(Arlasolve$^R$ DMI) | 90 |
| | TWEEN 20 | 40 |
| | NIKKOL HCO-50 | 80 |
| | NIKKOL VF-E | 40 |
| | MIGLYOL 812 | 10 |
| | MONOMULS 90-018 | 15 |
| | Total | 300 mg |
| Example 4 | | |
| 4-1. | Cyclosporin | 25 |
| | Dimethylisosorbide(Arlasolve$^R$ DMI) | 90 |
| | TWEEN 20 | 42 |
| | NIKKOL HCO-50 | 68 |
| | NIKKOL VF-E | 30 |
| | MIGLYOL 812 | 5 |
| | MONOMULS 90-018 | 5 |
| | Total | 265 mg |
| 4-2. | Cyclosporin | 25 |
| | Dimethylisosorbide(Arlasolve$^R$ DMI) | 90 |
| | TWEEN 20 | 42 |
| | NIKKOL HCO-50 | 68 |
| | NIKKOL VF-E | 40 |
| | MIGLYOL 812 | 10 |
| | MONOMULS 90-018 | 10 |
| | Total | 285 mg |
| 4-3. | Cyclosporin | 25 |
| | Dimethylisosorbide(Arlasolve$^R$ DMI) | 90 |
| | TWEEN 20 | 42 |
| | NIKKOL HCO-50 | 68 |
| | NIKKOL VF-E | 40 |
| | MIGLYOL 812 | 10 |
| | MONOMULS 90-018 | 20 |
| | Total | 295 mg |
| 4-4. | Cyclosporin | 25 |
| | Dimethylisosorbide(Arlasolve$^R$ DMI) | 90 |

| Component | Content (mg/Cap.) |
|---|---|
| TWEEN 20 | 42 |
| NIKKOL HCO-50 | 68 |
| NIKKOL VF-E | 40 |
| MIGLYOL 812 | 20 |
| MONOMULS 90-018 | 10 |
| Total | 295 mg |

Example 5

| | Component | Content (mg/Cap.) |
|---|---|---|
| 5-1. | Cyclosporin | 25 |
| | Dimethylisosorbide(Arlasolve$^R$ DMI) | 90 |
| | TWEEN 40 | 42 |
| | NIKKOL HCO-50 | 68 |
| | NIKKOL VF-E | 40 |
| | MIGLYOL 812 | 10 |
| | MONOMULS 90-018 | 15 |
| | Total | 290 mg |
| 5-2. | Cyclosporin | 25 |
| | Dimethylisosorbide(Arlasolve$^R$ DMI) | 50 |
| | TWEEN 60 | 42 |
| | NIKKOL HCO-50 | 68 |
| | NIKKOL VF-E | 40 |
| | MIGLYOL 812 | 10 |
| | MONOMULS 90-018 | 15 |
| | Total | 250 mg |
| 5-3. | Cyclosporin | 25 |
| | Dimethylisosorbide(Arlasolve$^R$ DMI) | 120 |
| | TWEEN 80 | 42 |
| | NIKKOL HCO-50 | 68 |
| | NIKKOL VF-E | 40 |
| | MIGLYOL 812 | 10 |
| | MONOMULS 90-018 | 15 |
| | Total | 320 mg |
| 5-4. | Cyclosporin | 25 |
| | Dimethylisosorbide(Arlasolve$^R$ DMI) | 50 |
| | TWEEN 81 | 80 |
| | NIKKOL HCO-50 | 68 |
| | NIKKOL VF-E | 40 |
| | MIGLYOL 812 | 10 |
| | MONOMULS 90-018 | 15 |
| | Total | 288 mg |

Example 6

| | Component | Content (mg/Cap.) |
|---|---|---|
| 6-1. | Cyclosporin | 25 |
| | Dimethylisosorbide(Arlasolve$^R$ DMI) | 90 |
| | TWEEN 20 | 42 |
| | NIKKOL HCO-40 | 68 |
| | NIKKOL VF-E | 40 |
| | MIGLYOL 812 | 10 |
| | MONOMULS 90-018 | 15 |
| | Total | 290 mg |
| 6-2. | Cyclosporin | 25 |
| | Dimethylisosorbide(Arlasolve$^R$ DMI) | 90 |
| | TWEEN 40 | 42 |
| | NIKKOL HCO-60 | 68 |
| | NIKKOL VF-E | 40 |
| | MIGLYOL 812 | 10 |
| | MONOMULS 90-018 | 15 |
| | Total | 290 mg |

Example 7

| | Component | Content (mg/Cap.) |
|---|---|---|
| 7-1. | Cyclosporin | 25 |
| | Dimethylisosorbide(Arlasolve$^R$ DMI) | 90 |
| | TWEEN 20 | 42 |
| | NIKKOL HCO-50 | 68 |
| | Isopropyl myristate | 40 |
| | MIGLYOL 812 | 10 |
| | MONOMULS 90-018 | 15 |
| | Total | 290 mg |
| 7-2. | Cyclosporin | 25 |
| | Dimethylisosorbide(Arlasolve$^R$ DMI) | 90 |
| | TWEEN 40 | 42 |
| | NIKKOL HCO-50 | 68 |
| | Isopropyl myristate | 40 |
| | MIGLYOL 812 | 10 |
| | MONOMULS 90-018 | 15 |
| | Total | 290 mg |
| 7-3. | Cyclosporin | 25 |
| | Dimethylisosorbide(Arlasolve$^R$ DMI) | 90 |
| | TWEEN 40 | 42 |
| | NIKKOL HCO-50 | 68 |
| | Ethyl oleate | 40 |
| | MIGLYOL 812 | 10 |
| | MONOMULS 90-018 | 15 |
| | Total | 290 mg |

The compositions of Examples 1 to 7 were prepared by dissolving cyclosporin in dimethylisosorbide as the cosurfactant, uniformly mixing the resulting solution with the remaining components and then introducing the microemulsion concentrate thus obtained into a machine for preparation of soft capsules according to the conventional method to prepare the desired soft capsule.

EXAMPLE 8

The bioavailability of the microemulsion prepared in Example 1—1 by using dimethylisosorbide cosurfactant according to the present invention as the test preparation was compared with the bioavailability of the commercial product containing ethanol, SANDIMMUN$^R$ Capsule, as the control preparation to estimate the influence of the novel dimethylisosorbide-containing preparation on the bioavailability of cyclosporin and its difference between respective subjects.

In this experiment, both of the test preparation and the control preparation were administered in an amount of 300 mg as cyclosporin per kg of rabbit.

Rabbits were uniformly fed with the conventional rabbit solid feed composition for 4 days or more under the same condition in wire cages. When the oral preparations were administered, rabbits were fasted for 48 hours in a restraint cage made of steel, during which rabbits were allowed to freely take water. Levin's tube having a diameter of 5 mm was interposed by the depth of 30 cm through the esophagus after the surface of the Levin's tube was coated with vaseline in order to reduce friction. Each of the test preparation and the control preparation was emulsified with 50 ml of water and then introduced into a syringe which is attached to the Levin's tube. Ear veins of rabbit were dilated using xylene and then blood was taken from each rabbit's ear vein before the test and after 0.5, 1, 1.5, 2, 3, 4, 6, 10 and 24 hours by means of heparin-treated disposable syringe. To 1 ml of blood thus obtained were added 0.5 ml of aqueous saturated sodium chloride solution and 2 ml of ether, and then the mixture was shaken for 5 minutes and centrifuged with 5000 rpm for 10 minutes to separate the supernatant (ether layer). 1 ml of the supernatant was collected and then developed in an activated silica sep-pak$^R$ (Waters). The developed sep-pak was washed with 5 ml of n-hexane and eluated with 2 ml of methanol. The eluate was evaporated to dryness in nitrogen gas under reduced pressure. The residue was analyzed by means of HPLC (High Performance Liquid Chromatography) [HPLC condition: column μ-Bondapak$^R$C$_{18}$ (Waters), mobile phase $CH_3CN:MeOH:H_2O=55:15:30$, detection 210 nm, flow rate 1.0 ml/min., column temperature 70° C., sensitivity 0.01 Aufs, injection volume 100 μl].

Figure 1:
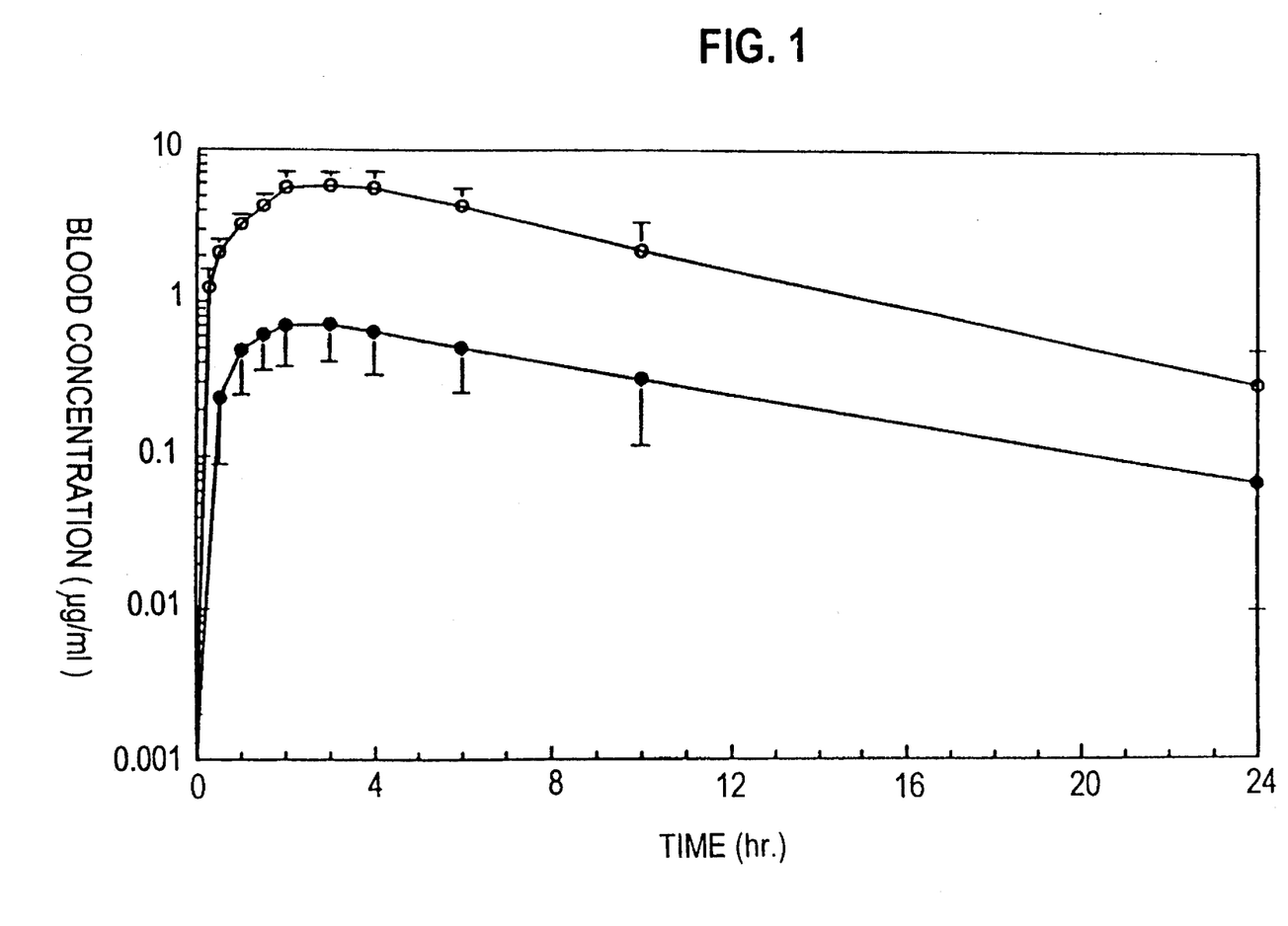
FIG. 1 is a graph showing the bioavailability of the cyclosporin soft capsule according to the present invention (-○-) in comparison with that of the commercial product, SANDIMMUN$^R$ Capsule (-●-)

The results are illustrated at FIG. 1 and the following Table 1.

TABLE 1

Bioavailability of the test preparation of the present invention and the commercial product (SANDIMMUN[R])

| Parameter | Control Prep. (A) | | Test Prep. (B) | | P(B/A) |
|---|---|---|---|---|---|
| | M ± S.D. (n = 6) | CV % (S.D./M) | M ± S.D (n = 6) | CV % (S.D./M) | |
| AUC (μg·hr/ml) | 13.5 ± 9.9 | 73.3% | 55.0 ± 17.7 | 32.2% | 4.1 |
| $C_{max}$ (μg/ml) | 0.8 ± 0.3 | 37.5% | 6.0 ± 1.5 | 25.0% | 7.5 |

Note:
Auc = Area under the blood concentration curve
$C_{max}$ = Maximum blood concentration of cyclosporin
M ± S.D. = Mean value ± Standard deviation
CV = Ratio of standard deviation to mean value
P(B/A) = Ratio of mean value of the test preparation to mean value of the control preparation As can be seen from the above table, the test preparation shows the increased AUC and $C_{max}$ values which are about 4 times or more and about 7 times or more, respectively, as high as those of the control preparation. Accordingly, it can be identified that the bioavailability of the test preparation is significantly increased in comparison with that of the control preparation. In addition, the test preparation of the present invention exhibits an effect of decreasing the difference between respective test subjects (CV %) by about 2 times or more in AUC value and by about 1.5 times in $C_{max}$ value, in comparison with the control preparation.

Accordingly, it could be determined that when the soft capsule composition according to the present invention is administered per oral, it shows the increased bioavailability of cyclosporin about 4 times as high as that of the prior commercial product containing ethanol, SANDIMMUN[R] Capsule and also a decrease of the difference between cyclosporin bioavailabilities in respective subjects, and at the same time, stably retains without any change during the long term storage. Thus, it is apparent that the microemulsion concentrate according to the present invention provides a significant improvement in the field of preparation of cyclosporin soft capsules.

EXAMPLE 9

The membrane permeation property of the cosurfactant over the storage period at the room temperature was examined for the soft capsules prepared in Example 1—1 by using dimethylisosorbide (Arlasolve[R] DMI) as a cosurfactant according to the present invention and the commercial product, SANDIMMUN[R] soft capsule, which contains ethanol as the cosurfactant and then the storage stabilities of two preparations were compared. The content of the cosurfactant in each soft capsule preparation was analyzed by gas chromatography.

The experiment results are given in the following Table 2.

TABLE 2

Change in the contents of the cosurfactants contained in soft capsules over the storage period

| | Content (per cap.) | | | |
|---|---|---|---|---|
| | Initial | Storage period (days) | | |
| Cosurfactant | content | 1 | 5 | 10 |
| Dimethylisosorbide (Test preparation) | 31.0 (100.0%) | 29.2 (94.2%) | 28.7 (92.6%) | 28.3 (91.3%) |
| Ethanol (Control preparation) | 10.8 (100.0%) | 7.8 (72.2%) | 3.8 (35.2%) | 3.0 (27.8%) |

Note:
Conditions of gas chromatography for each cosurfactant
1) Dimethylisosorbide-
Column: Ultra 2 (Cross-linked 2% phenylmethyl silicone gun phase, 25 m × 0.32 mm, thickness 0.52 μm)
Column temperature: 230° C. (Isothermal)
Detector: FID (Temperature: 270° C.)
Injection temperature: 275° C.
Carrier gas: He (Partition ratio 80:1)
Injection volume: 5 μl
Internal standard: Octyl alcohol
2) Ethanol-
Column: HP-20M (Carbowax 20M) (25 m × 0.32 mm, film thickness 0.3 μm)
Column temperature: 30° C. (Isothermal)
Detector: FID (Temperature: 200° C.)
Injection temperature: 150° C.
Carrier gas: He (Partition ratio 80:1)
Injection volume: 5 μl
Internal standard: Diethyl ether As can be seen from the results described in the above Table 2, dimethylisosorbide used as a cosurfactant according to the present invention does not change in its content even after 10 days while ethanol cosurfactant used in the prior art was reduced by 27.8% of the initial content after 10 days. Accordingly, it can be readily determined that in the cyclosporin soft capsule using dimethylisosorbide as a cosurfactant according to the present invention since dimethylisosorbide does not volatilize during the storage period and is stably retained in the composition, the active ingredient cyclosporin is maintained in the stable solution and therefore its bioavailability can be consistently high.

EXAMPLE 10

To determine the particle-size distribution of the microemulsions which are formed by diluting the cyclosporin soft capsule composition of the present invention, which is prepared by using dimethylisosorbide (Arlasolve[R] DMI) as a cosurfactant according to Example 1–2, and the commercial product SANDIMMUN[R] with water the microemulsions prepared therefrom were analyzed by means of a particle size analyzer (see Terence Allen Ph.D., Particle Size Measurement, Chapman and Hall, London, New York, 3rd Ed.). The results are shown in FIGS. 2 (SANDIMMUN[R]) and 3 (the composition of the present invention prepared according to Example 1–2).

Figure 2:
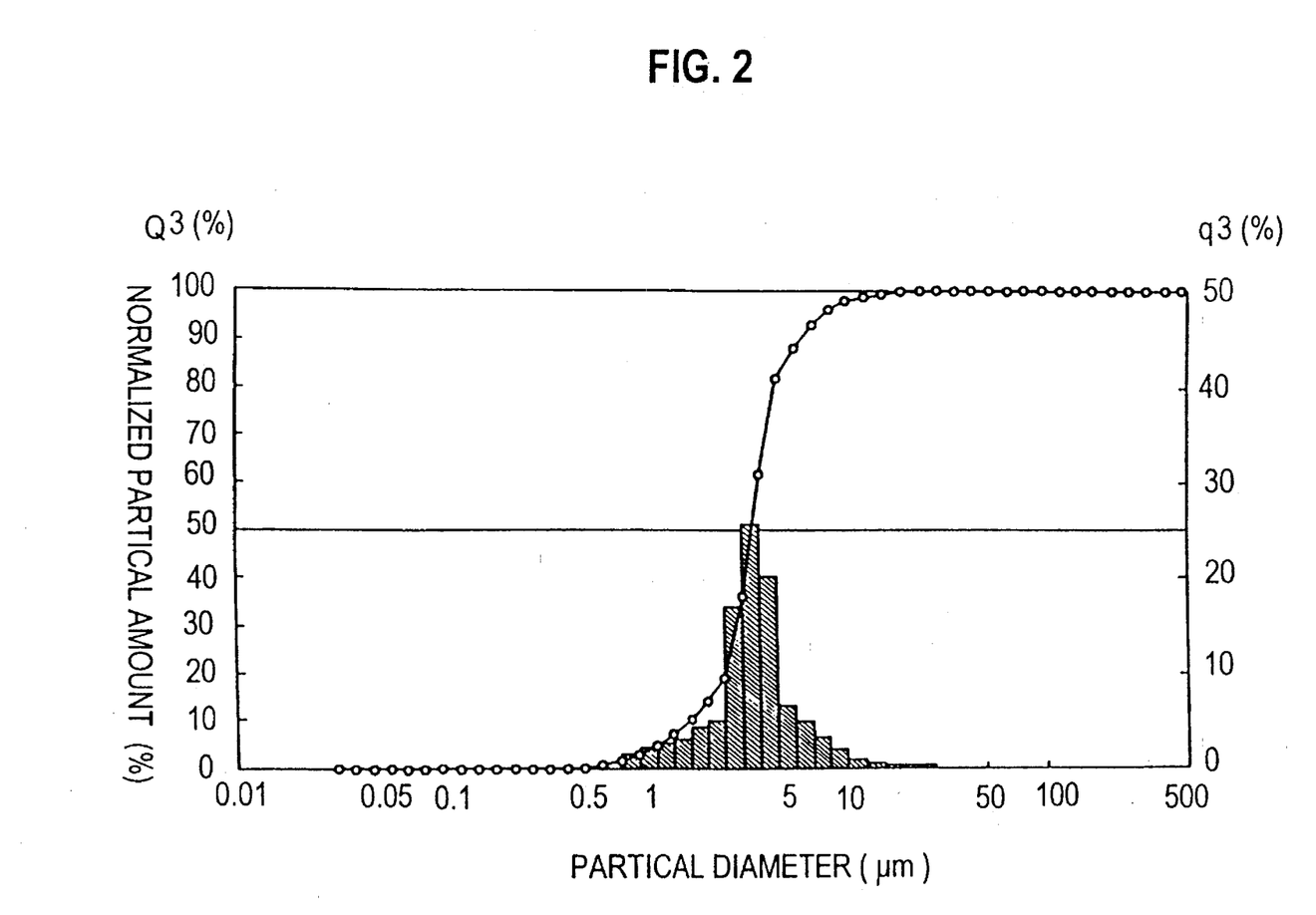
FIG. 2 is a graph showing the particle-size distribution of the emulsion formed from the commercial product SANDIMMUN$^R$.
Figure 3:
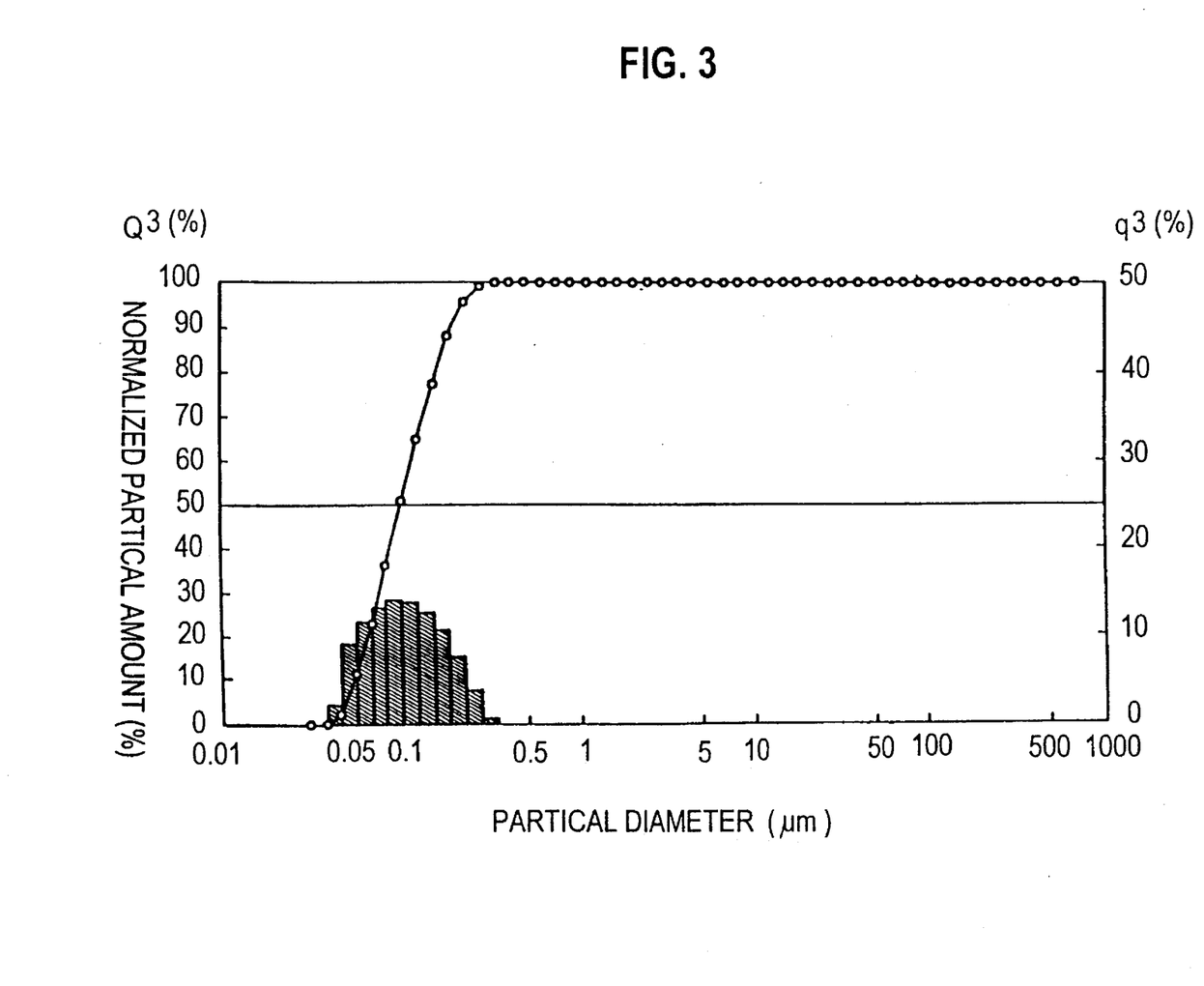
FIG. 3 is a graph showing the particle-size distribution of the emulsion formed from the composition of the present invention prepared according to Example 1–2.

As can be seen from FIGS. 2 and 3, the average emulsified particle size of the preparation of Example 1–2 was about 0.1 μm and the average particle size of the commercial product SANDIMMUN[R] soft capsule was 3.3 μm. Thus, it can be seen that the composition of the present invention can form the microemulsion having more micronized emulsified particle in comparison with the commercial product SANDIMMUN[R]. This result corresponds to that of Example 8 which demonstrates that the composition of the present invention provides a significantly increased bioavailability and a decrease of the difference between bioavailabilities in respective subjects. Accordingly, it is apparent that the composition of the present invention shows a significant improvement over the conventional commercial products in view of their emulsified state.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A cyclosporin soft capsule composition comprising cyclosporin as an active ingredient, dimethylisosorbide as a cosurfactant, one or more components selected from the group consisting of an esterified compound of fatty acid and primary alcohol, medium chain fatty acid triglyceride and fatty acid monoglyceride as an oil component, and a surfactant having an HLB (Hydrophilic-lipophilic balance) value of 10 to 17.

2. The cyclosporin soft capsule composition of claim 1 wherein said cyclosporin is cyclosporin A.

3. The cyclosporin soft capsule composition of claim 1 wherein said esterified compound of fatty acid and primary alcohol is an esterified compound of fatty acid having 8 to 20 carbon atoms and primary alcohol having 2 to 3 carbon atoms.

4. The cyclosporin soft capsule composition of claim 3 wherein said esterified compound of fatty acid and primary alcohol is isopropyl myristate, isopropyl palmitate, ethyl linoleate or ethyl oleate.

5. The cyclosporin soft capsule composition of claim 4 wherein said esterified compound of fatty acid and primary alcohol is ethyl linoleate.

6. The cyclosporin soft capsule composition of claim 1 wherein said medium chain fatty acid triglyceride is caprylic/capric acid triglyceride.

7. The cyclosporin soft capsule composition of claim 1 wherein said fatty acid monoglyceride is a monoglyceride of oleic acid.

8. The cyclosporin soft capsule composition of claim 1 wherein said oil component is a mixture of two or more components selected from the group consisting of the esterified compound of fatty acid and primary alcohol, medium chain fatty acid triglyceride and fatty acid monoglyceride.

9. The cyclosporin soft capsule composition of claim 8 wherein the weight ratio of the esterified compound of fatty acid and primary alcohol, medium chain fatty acid triglyceride and fatty acid monoglyceride is 1:0.12–0.5:0–0.5.

10. The cyclosporin soft capsule composition of claim 9 wherein the weight ratio of the esterified compound of fatty acid and primary alcohol, medium chain fatty acid triglyceride and fatty acid monoglyceride is 1:0.25:0.375.

11. The cyclosporin soft capsule composition of claim 8 wherein the total fatty acids have the ratio of caprylic acid:capric acid:palmitic acid:oleic acid:linoleic acid:ricinoleic acid of 3–7:3–7:5–8:15–25:40–50:3–10.

12. The cyclosporin soft capsule composition of claim 1 wherein said surfactant is a polyoxyethylene product of hydrogenated vegetable oil or a polyoxyethylene-sorbitan-fatty acid ester.

13. The cyclosporin soft capsule composition of claim 12 wherein said surfactant is a mixed surfactant consisting of NIKKOL HCO-50 and TWEEN 20 in the ratio of 1:0.5–2.

14. The cyclosporin soft capsule composition of claim 13 wherein said surfactant is a mixed surfactant consisting of NIKKOL HCO-50 and TWEEN 20 in the ratio of 1:1.0.

15. The cyclosporin soft capsule composition of claim 1 wherein said cyclosporin, said dimethylisosorbide, said oil component and said surfactant are present in the ratio of 1:1–5:1–5:3–6.

16. The cyclosporin soft capsule composition of claim 15 wherein said cyclosporin, said dimethylisosorbide, said oil component and said surfactant are present in the ratio of 1:3–4:1.5–3:4–6.

17. The cyclosporin soft capsule composition of claim 16 wherein said cyclosporin, said dimethylisosorbide, said oil component and said surfactant are present in the ratio of 1:3.6:2.6:5.5.

18. The cyclosporin soft capsule composition of claim 1 further including a pharmaceutically acceptable additive therefor.

19. A soft capsule composition comprising cyclosporin, dimethylisosorbide, one or more components selected from the group consisting of an esterified compound of fatty acid and primary alcohol, medium chain fatty acid triglyceride and fatty acid monoglyceride, and a surfactant having an HLB value of 10 to 17.

* * * * *